(12) United States Patent
Ishikawa

(10) Patent No.: US 11,890,423 B2
(45) Date of Patent: Feb. 6, 2024

(54) HEALTHCARE DEVICE AND A METHOD OF USE THEREOF

(71) Applicant: Kenji Ishikawa, San Mateo, CA (US)

(72) Inventor: Kenji Ishikawa, San Mateo, CA (US)

(*) Notice: Subject to any disclaimer, the term of this patent is extended or adjusted under 35 U.S.C. 154(b) by 0 days.

(21) Appl. No.: 17/942,897

(22) Filed: Sep. 12, 2022

(65) Prior Publication Data
US 2023/0096995 A1    Mar. 30, 2023

Related U.S. Application Data

(60) Provisional application No. 63/247,977, filed on Sep. 24, 2021.

(51) Int. Cl.
*A61M 21/00* (2006.01)
*A61M 21/02* (2006.01)
*A61F 7/00* (2006.01)

(52) U.S. Cl.
CPC .............. *A61M 21/00* (2013.01); *A61F 7/007* (2013.01); *A61M 2021/0066* (2013.01); *A61M 2205/3368* (2013.01); *A61M 2205/3606* (2013.01); *A61M 2210/10* (2013.01)

(58) Field of Classification Search
CPC .......... A61M 21/00; A61M 2021/0066; A61M 2205/3368; A61M 2205/3606; A61M 2210/10; A61F 7/007
See application file for complete search history.

(56) References Cited

U.S. PATENT DOCUMENTS

| 4,585,002 A * | 4/1986 | Kissin | ..................... A61F 7/007 607/96 |
| 2018/0369064 A1* | 12/2018 | Baxter | ....................... A61F 7/02 |
| 2020/0050248 A1* | 2/2020 | Smith | ................... H05B 1/0227 |
| 2021/0059325 A1* | 3/2021 | Yazawa | ............... A41D 13/0051 |

* cited by examiner

*Primary Examiner* — Thaddeus B Cox
*Assistant Examiner* — Joshua Daryl D Lannu
(74) *Attorney, Agent, or Firm* — Barry Choobin; Patent 360

(57) ABSTRACT

A device and method for inducing sleep, improving blood circulation, and correcting autonomous imbalances. The device includes a heat exchange member mounted on top of housing, the heat exchange member can receive a neck of a user and apply alternate hot and cold stimuli to the neck. The hot and cold stimuli improve blood circulation and correct the autonomous imbalances. The device includes a drive module and a heat sink to quickly switch from hot to cold.

10 Claims, 3 Drawing Sheets

HEALTHCARE DEVICE AND A METHOD OF USE THEREOF

CROSS-REFERENCE TO RELATED APPLICATIONS

This application claims priority from a U.S. Provisional Patent Appl. No. 63/247,977 filed on Sep. 24, 2021, which is incorporated herein by reference in its entirety.

FIELD OF INVENTION

The present invention relates to a healthcare device and a method of use thereof, and more particularly, the present invention relates to a healthcare device and use thereof to induce sleep and improve blood circulation.

BACKGROUND

Good sleep is essential for staying healthy. Lack of enough sleep can make a person feel tired all day. Chronic lack of quality sleep can deteriorate health affecting physical and mental well-being and daily functioning. A person may lack good sleep for a variety of reasons or disorders. Insomnia is a most common sleep disorder in which a person is unable to fall asleep and stay asleep.

Several therapies are known in the art of inducing sleep. Medications, such as hypnotics are available, however, the medications themselves have many side effects and are habit-forming. Physical and mental exercises are also known in the art that helps in inducing sleep, however, such exercises are complex to practice and often ineffective.

A need is therefore appreciated for a device and method to induce sleep and improve sleep patterns and overall health.

SUMMARY OF THE INVENTION

The following presents a simplified summary of one or more embodiments of the present invention to provide a basic understanding of such embodiments. This summary is not an extensive overview of all contemplated embodiments and is intended to neither identify critical elements of all embodiments nor delineate the scope of any or all embodiments. Its sole purpose is to present some concepts of one or more embodiments in a simplified form as a prelude to the more detailed description that is presented later.

The principal object of the present invention is therefore directed to a healthcare device and a method for inducing sleep.

It is another object of the present invention to have negligible side effects.

It is still another object of the present invention that the method is not habit-forming.

It is a further object of the present invention to improve overall health.

It is yet another object of the present invention that the method is easy to use.

In one aspect, disclosed is a device and a method for inducing sleep, improving blood circulation, and correcting autonomous imbalances. The device comprising a housing; a heat exchange member mounted on a top of the housing, the heat exchange member is ergonomically designed to receive a neck of a user and apply alternate hot and cold stimuli to the neck; and a heat sink and a fan to quickly dissipate the heat. The device quickly switches from hot to cold using the heat sink. The device switches from hot to cold in about 25 seconds. The device comprises a drive module for heating the heat exchange member. The drive module and the heat sink are configured to keep the heat exchange member at 106° F. for about 40 seconds, and thereafter cool down to 64° F. within about 25 seconds and keep the heat exchange member at 64° F. for about 30 seconds. The drive module and the heat sink are configured to keep the heat exchange member at 64° F. for about 40 seconds, and thereafter warm up to 106° F. within about 25 seconds and keep the heat exchange member at 106° F. for about 30 seconds.

BRIEF DESCRIPTION OF THE DRAWINGS

The accompanying figures, which are incorporated herein, form part of the specification and illustrate embodiments of the present invention. Together with the description, the figures further explain the principles of the present invention and enable a person skilled in the relevant arts to make and use the invention.

DETAILED DESCRIPTION

Figure 1:
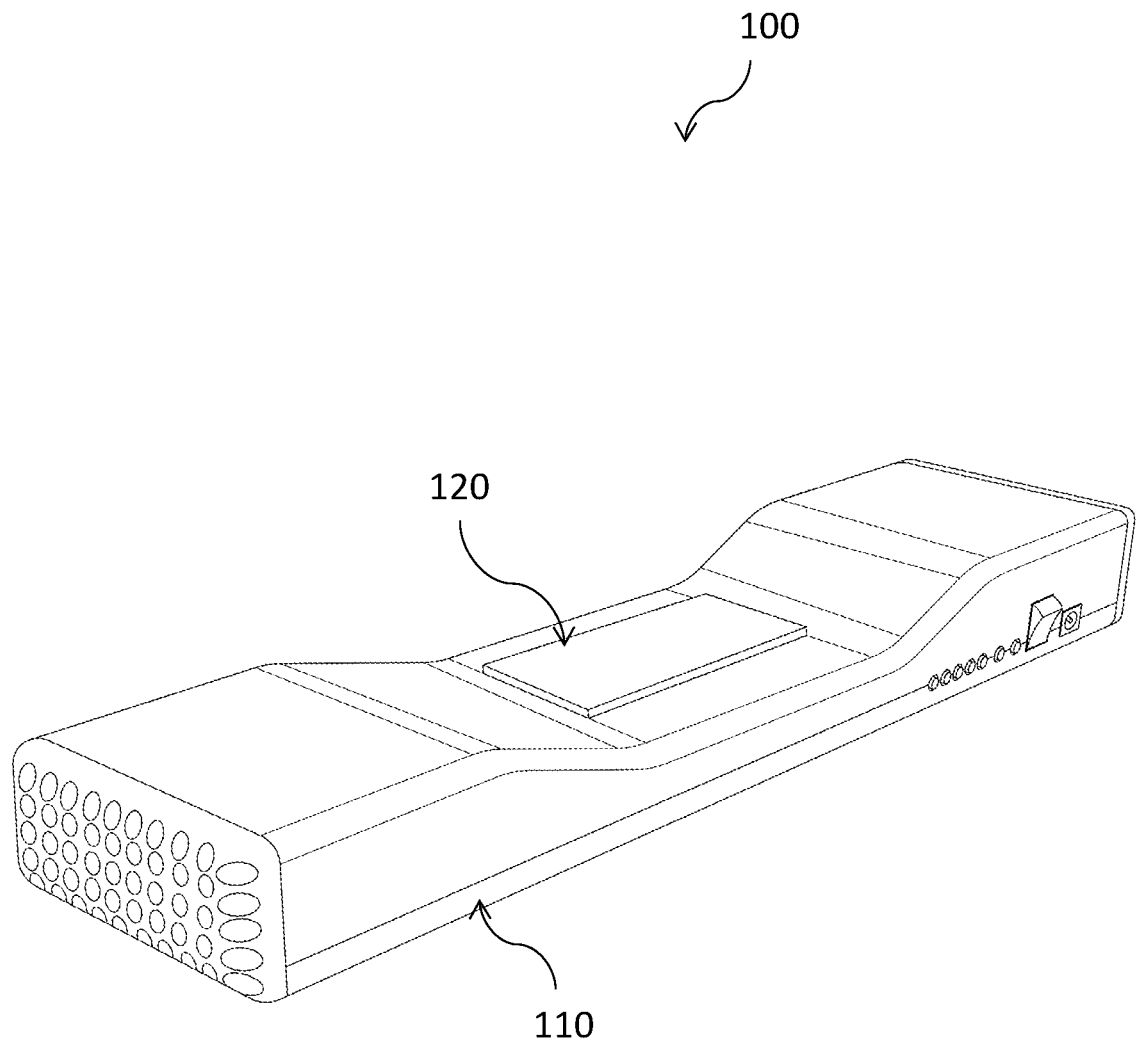
FIG. 1 is a perspective view of the device, according to an exemplary embodiment of the present invention.

Subject matter will now be described more fully hereinafter. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, reasonably broad scope for claimed or covered subject matter is intended. Among other things, for example, the subject matter may be embodied as apparatus and methods of use thereof. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is to describe particular embodiments only and is not intended to be limiting to embodiments of the invention. As used herein, the singular forms "a", "an" and "the" are intended to include the plural forms as well, unless the context indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely to illustrate the general principles of the invention since the scope of the invention will be best defined by the allowed claims of any resulting patent.

The following detailed description is described with reference to the drawings, wherein like reference numerals are used to refer to like elements throughout. In the following description, for purposes of explanation, specific details may be set forth in order to provide a thorough understanding of the subject innovation. It may be evident, however, that the claimed subject matter may be practiced without these specific details. In other instances, well-known structures and apparatus are shown in block diagram form in order to facilitate describing the subject innovation. Moreover, the drawings may not be to scale.

Disclosed are a device and a method of use thereof for inducing sleep, improving blood circulation, correcting any autonomous imbalance condition, and improving overall health. Correcting any autonomous imbalance condition can decrease stress and anxiety, resulting in good and natural sleep. Disturbances in circadian rhythm can be corrected and a person can take natural quality sleep. The disclosed device can apply alternative hot and cold stimuli on the back of the neck that can affect good blood circulation and correct any autonomous system imbalances which induce sleep and improve optimum health. Sleep is affected by correcting the autonomous balance system which improves overall good health, and a person can take natural sleep. Sleep disorders and sleep-obsessed conditions can be resolved by regular use of the disclosed device.

Regular use of the disclosed device can activate the autonomic nerves, as well as affect good switching balance between sympathetic and parasympathetic nerves effectively. The disclosed device can target the nerves located behind the skin at the back of the neck.

It is an advantage that the disclosed device can restore a balanced autonomic system. A balanced autonomic system includes Relax/sleeping time (night): Parasympathetic nerve is bigger than Sympathetic nerves, and Active time (day): Parasympathetic nerves are lower than Sympathetic nerves. With regular use of the disclosed device, the balance of the autonomous system and circadian rhythm can be restored, which allows a user to take natural and healthy sleep.

Referring to FIG. 1 shows an exemplary embodiment of the disclosed device 100. The device 100 can include a housing 110 that encases most of the components of the disclosed device and also provides an aesthetic appearance to the device. The housing may also protect the device from dirt and external shocks. The housing can be made from an insulative material, such as plastic that prevents any charge build-up and avoids the risk of electric shock. The housing can be thin, narrow, and elongated in dimensions. The housing can have a flat base that allows the device to be stably placed on a flat surface, such as a mattress. The thin profile of the device allows the device to be placed under the neck without any discomfort to the user. The user can lie down on the bed with the device placed on the mattress and under the neck. It is understood, however, that the device can be placed on the neck while the user is sitting without departing from the scope of the present invention.

On top of the housing can be mounted a heat exchange member 120. The heat exchange member can be ergonomically designed to match the shape of the neck, such as maximum contact can be established between the back of the neck effectively and the heat exchange member. The heat exchange member can include a suitable ergonomically designed exterior for comfort and to prevent any injury due to hard edges. The heat exchange member can be made from a material that allows uniform dissipation of heat for quickly changing the temperature between hot and cold over the neck of the user and prevents any localized chills or hot flashes. This rapid change (about 25 seconds) between hot and cold temperatures is an especially essential element for autonomic nervous stimuli.

The heat exchange member can be alternatively heated and cooled by a custom-designed heatsink and fan, the heat exchange member can be alternatively heated at a predetermined frequency, and thus the alternative hot and cold stimulus can be applied to the back of the neck. The heat exchange member can be driven by a drive module for alternate heating and cooling. The device can be powered through a power supply and using an AC to DC adapter.

The disclosed device can also include an Arduino module that can control the heating. The drive module can save pre-determined hot and cold temperatures for the stimulation therapy to the neck of the user. As shown in FIG. 1, the device can include buttons for selecting the saved temperatures as modes.

Figure 2:
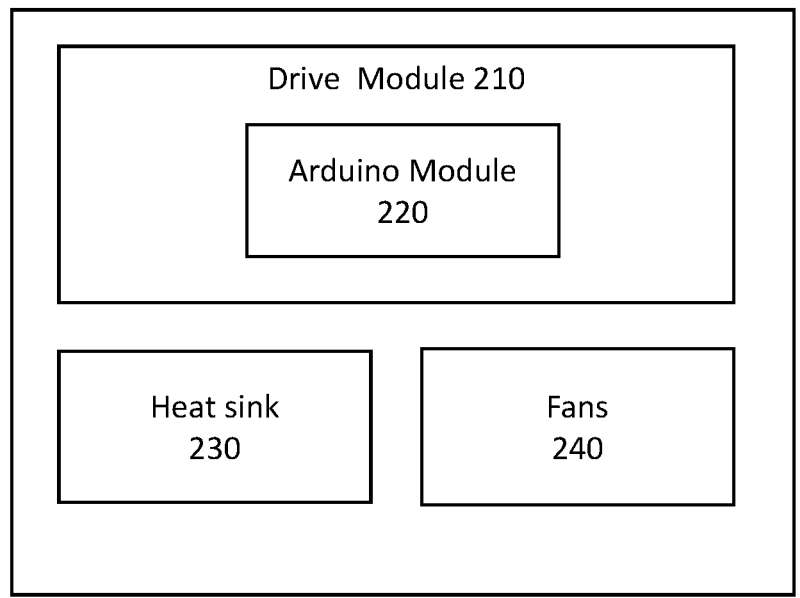
FIG. 2 is a block diagram showing components of the device, according to an exemplary embodiment of the present invention.

Referring to FIG. 2, shows a block diagram of the disclosed device that includes a drive module 210 to control the disclosed device including setting hot and cold temperatures, operating heatsink and fans, quickly and effectively switching formations, and tuning on/off automatically. The device further includes an Arduino module 220 to control power circuitry including a security fuse system. A specially designed heat sink 230 and a fan 240 to dissipate heat can also be incorporated.

Figure 3A:
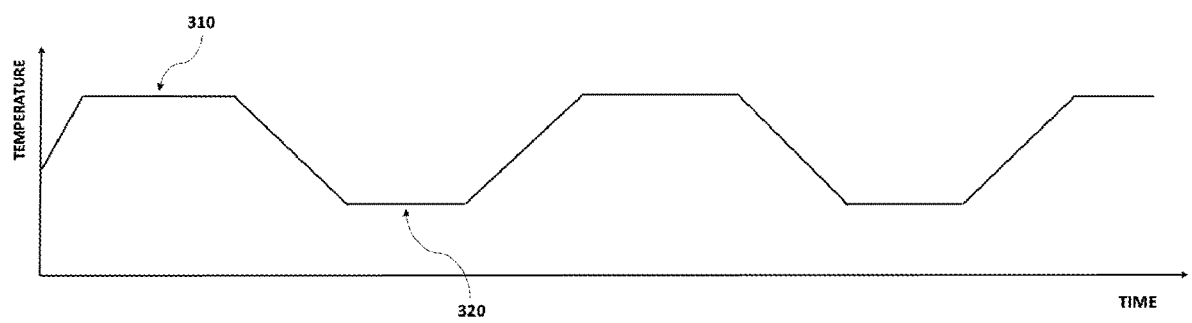
FIGS. 3A and FIG. 3B show hot and cold stimulus patterns, according to an exemplary embodiment of the present invention.
Figure 3B:
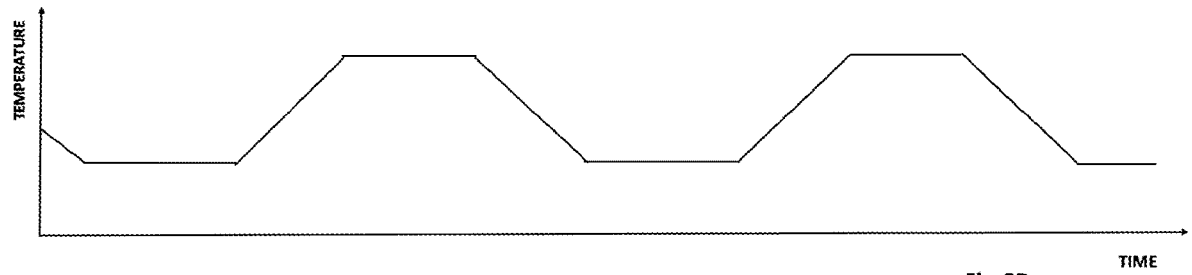

Referring to FIGS. 3A and 3B shows a therapy cycle for alternative hot and cold stimulus. The disclosed device can heat up to a peak high temperature 310 and cool down to a peak low temperature 320. The peak high temperature, the peak low temperature, and the duration between the peak high temperature and the peak low temperature can be fixed. The peak high temperature and the peak low temperature may not be absolute but can vary within certain limits, such as within two degrees of temperature. One peak high temperature and adjacent peak low temperature can form one cycle and such cycles can be repeated to apply the alternative hot and cold stimulus for a predefined duration. FIG. 3A (mode #1) shows a pattern of alternative cycles of hot and cold stimuli. The duration between the peak low temperature of a cycle and the peak high temperature of an adjacent cycle can also be varied which may be the same or different than the duration (about 25 seconds) between the peak high temperature and the peak low temperature of the same cycle. Moreover, the peak high temperatures and the peak low temperatures of different cycles in the same therapy can also be varied. FIG. 3B (mode #2) shows a variation in the cycle in which the peak temperatures are maintained for a pre-defined duration and this pre-defined duration can be varied without departing from the scope of the present invention.

In one implementation, four different profiles/Modes can be provided i.e., 1, 2, 3, and 4 to choose from. Mode 1: Start hot temperature (106° F.) for 40" and change quickly (about 25") to the cold temperature (64° F.) for 30" for every 7 times alternately and automatically finished. Mode 2: Start cold temperature (64° F.) for 40" and change quickly (about 25") to the hot temperature (106° F.) for 30" for every 7 times alternately and automatically finished. Mode 3: Start/keep Hot temperature (106° F.) along for 360" for use in wintertime for warming body. Mode 4: Start/keep Cold temperature (64° F.) along for 360" for use in the summertime for cooling down body heats.

This device works to instantly induce a short sleep but also in the long term it works to improve autonomic nerve condition (set healthy daily circadian balance with sympathetic and parasympathetic nerves).

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A device for inducing sleep and improving blood circulation, the device comprising:
    a housing;
    a heat exchange member mounted on a top of the housing, wherein the heat exchange member is configured to contact at least a neck of a user, and apply alternate hot and cold stimuli in predetermined intervals to the neck;
    a heat sink and a fan to quickly dissipate heat from the heat exchange member; and
    a drive module for controlling the heat exchange member based on the predetermined intervals, wherein the drive module is configured to keep the heat exchange member at 106° F. for about 40 seconds, and thereafter cool down to 64° F. within about 25 seconds and keep the heat exchange member at 64° F. for about 30 seconds.

2. The device according to claim 1, wherein the heat exchange member is configured to quickly switch from a hot state to a cold state using the heat sink and the fan.

3. The device according to claim 2, wherein the heat exchange member switches from the hot state to the cold state in about 25 seconds.

4. The device according to claim 1, wherein the drive module is further configured to keep the heat exchange member at 64° F. for about 40 seconds, and thereafter warm up to 106° F. within about 25 seconds and keep the heat exchange member at 106° F. for about 30 seconds.

5. The device according to claim 1, wherein the housing is rigid and has a flat base.

6. A method for inducing sleep, improving blood circulation, and correcting autonomous imbalances, the method comprising:
    providing a device comprising:
        a housing,
        a heat exchange member mounted on a top of the housing, wherein the heat exchange member is configured to contact at least a neck of a user and apply alternate hot and cold stimuli in predetermined intervals to the neck,
        a heat sink and a fan to quickly dissipate heat from the heat exchange member,
        a drive module for controlling the heat exchange member based on the predetermined intervals, wherein the drive module is configured to keep the heat exchange member at 106° F. for about 40 seconds, and thereafter cool down to 64° F. within about 25 seconds and keep the heat exchange member at 64° F. for about 30 seconds;
    placing the neck over the device; and
    applying alternate hot and cold stimuli to a back of the neck based on the predetermined intervals.

7. The method according to claim 6, wherein the heat exchange member is configured to quickly switch from a hot state to a cold state using the heat sink.

8. The method according to claim 7, wherein the heat exchange member switches from the hot state to the cold state in about 25 seconds.

9. The method according to claim 6, wherein the drive module is further configured to keep the heat exchange member at 64° F. for about 40 seconds, and thereafter warm up to 106° F. within about 25 seconds and keep the heat exchange member at 106° F. for about 30 seconds.

10. The method according to claim 6, wherein the housing is rigid and has a flat base.

* * * * *